United States Patent [19]

Grollimund

[11] Patent Number: 4,458,702
[45] Date of Patent: Jul. 10, 1984

[54] DENTAL FLOSSER
[76] Inventor: Everett C. Grollimund, 3306 Nuttree Woods Pl., Brandermill, Midlothian, Va. 23113
[21] Appl. No.: 385,808
[22] Filed: Jun. 7, 1982
[51] Int. Cl.³ ............................................. A61C 15/00
[52] U.S. Cl. .................................. 132/92 A; 132/91; 433/29; 15/22 R
[58] Field of Search ..................... 132/91, 92 R, 92 A, 132/79 E, DIG. 2; 128/62 A; 15/22 R, 22 A, 22 C, 167 R; 433/118, 142, 114, 29, 122, 123

[56] References Cited
U.S. PATENT DOCUMENTS

| | | | |
|---|---|---|---|
| 2,246,523 | 6/1941 | Kulik | 15/22 R |
| 3,028,614 | 4/1962 | Bristow | 15/22 R |
| 3,746,017 | 7/1973 | Casselman | 132/92 A |
| 3,886,956 | 6/1975 | Cash | 132/91 |
| 3,906,963 | 9/1975 | Jenkins et al. | 132/91 |
| 3,978,852 | 9/1976 | Annoni | 128/62 A |
| 4,235,253 | 11/1980 | Moore | 132/92 R |
| 4,245,658 | 1/1981 | Lecouturier | 132/92 A |
| 4,307,740 | 12/1981 | Florindez et al. | 132/92 R |

Primary Examiner—John J. Wilson

[57] ABSTRACT

Powered apparatus for cleaning teeth with dental floss, including arms extending from one end of the apparatus and mounted to rock about an axis transverse to the length of the apparatus, and a floss supply system including clamps operable to permit pulling floss through the arms and to tighten it in preparation for use, and to secure the tightened floss between the arms so that it may be used in cleaning between teeth.

7 Claims, 17 Drawing Figures

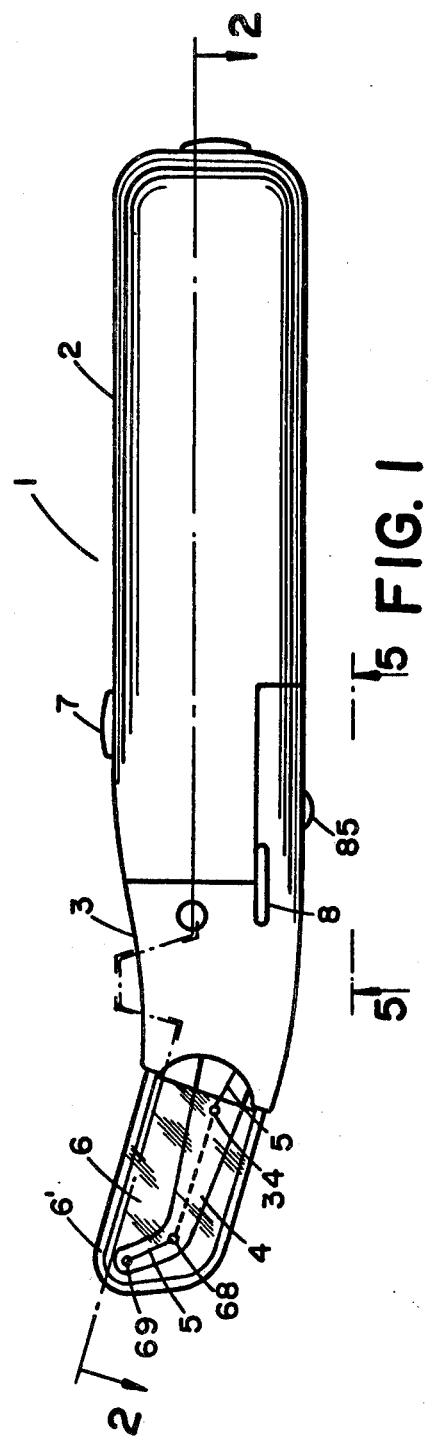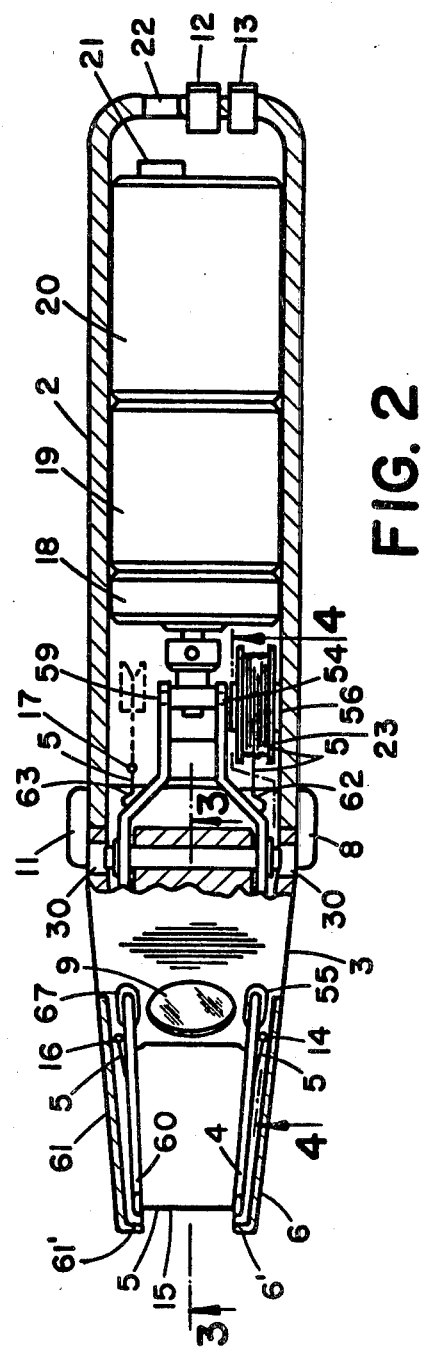

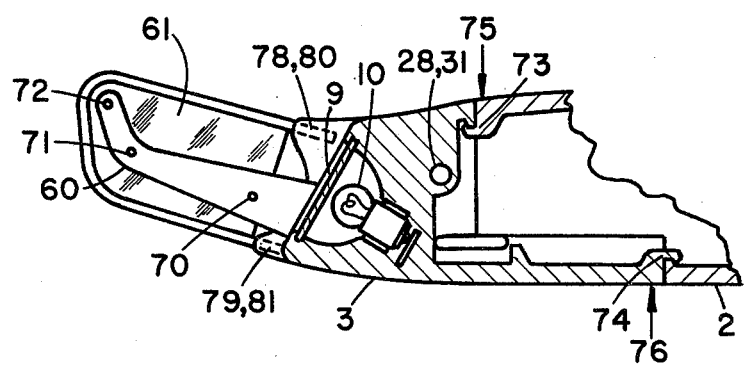
FIG. 3
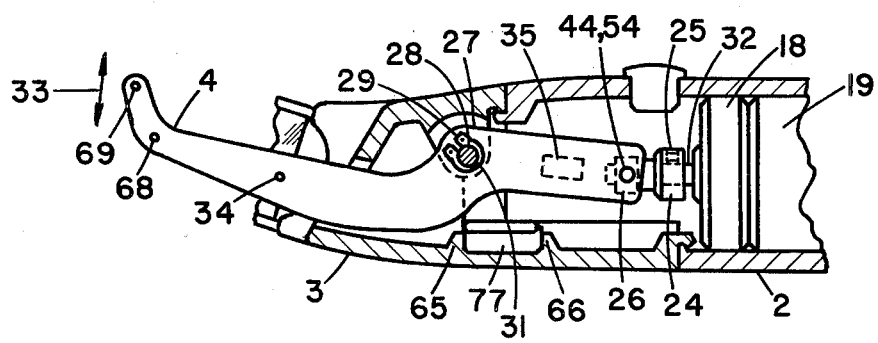
FIG. 4
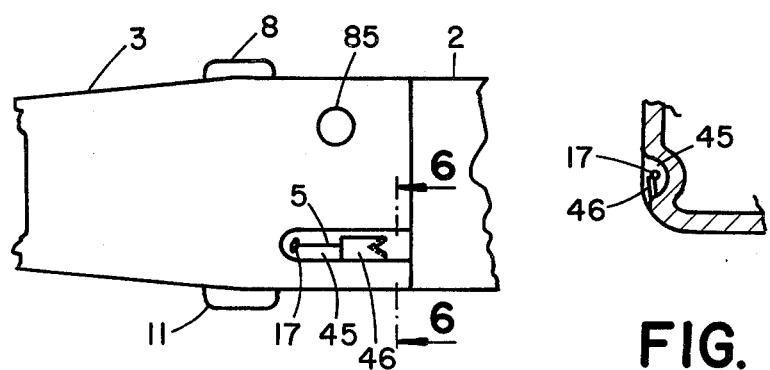
FIG. 5
FIG. 6

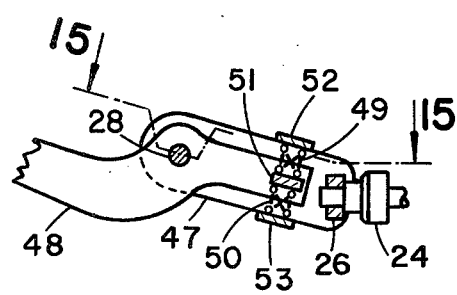
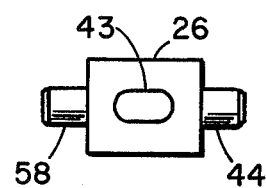
FIG. 14
FIG. 13
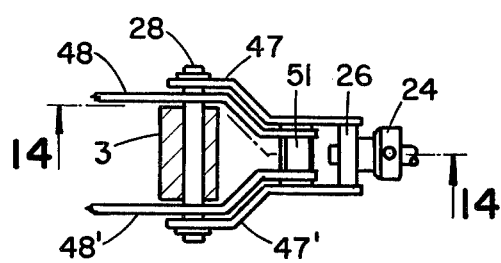
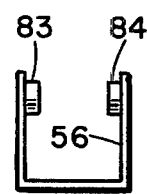
FIG. 15
FIG. 16
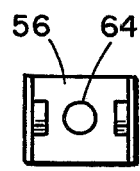
FIG. 17

DENTAL FLOSSER

BACKGROUND OF THE INVENTION

Dental flossing is ordinarily done manually, by holding a segment of dental floss between the fingers of two hands and moving an intermediate portion between a pair of teeth to clean their adjacent sidewalls by a vertical scraping motion, while trying to observe the operation in a mirror in a fixed mounting nearby. Flossing becomes difficult and awkward due to the manual dexterity a person needs in order to be effective and produce satisfactory results. Because of this difficulty and awkwardness many people become discouraged and discontinue flossing. Therefore, by providing a simplified means of dental flossing, more people will perform this task, thereby reducing and/or preventing dental caries and periodontal disease.

Various proposals for means to assist in this operation has been advanced, but apparently the only one to win substantial acceptance has been a Y shaped plastic tool to hold the floss between the ends of the two arms of the Y, while the base of the Y provides a handle for controlling movement of the floss. The two arms are curved downwardly to make it easier to insert the floss between the teeth. While this tool is useful, it does not provide any power assist in the operation.

Various designs have been proposed in the past for power-assisted flossing, such as those disclosed in U.S. Pat. Nos. 1,091,789 (Andren), 2,381,530 (Dembenski), 2,444,638 (Dobbins), 3,421,524 (Waters), 3,759,274 (Warner), 4,014,354 (Garrett), 4,235,253 (Moore), and 4,265,257 (Salyer). The structural and operational limitations of the devices disclosed in these patents were evidently such as to leave unsatisfied the public demand for a powered unit to assist in flossing of teeth. This is particularly a problem for those whose handicaps make conventional manual flossing difficult or impossible.

SUMMARY OF THE INVENTION

In accordance with the present invention, a hand held elongated body is provided with a pair of spaced arms projecting from one end of the body, and these arms are mounted within the body for pivotal movement about an axis extending transversely to the length of the body. Dental floss is extended between the ends of the arms. A motor in the body is connected to rock the arms on their transverse pivotal axis, and the distance between the suspended floss and the pivotal axis is long enough to substantially flatten the arc of limited oscillation of the arm ends where the floss is suspended. Consequently, a substantially straight up and down stroking movement of the suspended floss is achieved, with no end-wise movement of the floss. The floss is thus moved laterally in a substantially flat plane and substantially perpendicular to the central axis of the elongated body, and the motor is preferably provided with speed reducing gears to provide a relatively slow reciprocal movement of the floss. The speed is accordingly less than that resulting from direct drive fom a conventional electric motor, but faster (and with a shorter stroke) than in the case of manual cleaning.

As a further improvement, a resilient element may be introduced in the power drive to the arms, so that the floss may be caused to yield when it encounters resistance in excess of a predetermined range of resistance expected in cleaning teeth. Also, a light is preferably provided at the front end of the unit, to assist the user in seeing the area of the operation of the floss suspended between the action arms. Safety is further enhanced by a pressure switch which, when released, will automatically stop the drive motor.

Convenience and efficiency in using the unit of the invention is further enhanced by mounting a supply of floss in the body of the unit and by leading it past releasable clamps to the arms and back again to the body where means may be provided for cutting off the leading end of the floss and leaving an exposed cut portion which may be grasped to pull another supply of suspended floss between the arms, while holding the clamps open to permit this movement. The clamp controls assist in tightening the floss, and are mounted on a portion of the body where they will not be grasped while the pressure switch is being held down to activate the motor.

These and other features and advantages of the invention will become apparent as the following disclosure of present preferred practices of the invention proceed.

BRIEF DESCRIPTION OF THE DRAWINGS

Present preferred embodiments of the invention are shown, for purposes of illustration only, in the accompanying drawings in which:

FIG. 1 is a side view of a powered flossing unit embodying the invention;

FIG. 2 is a top view, partially broken away and sectioned upon the line 2—2 in FIG. 1, of the embodiment shown in FIG. 1;

FIG. 3 shows a section on the line 3—3 in FIG. 2, partially broken away to show only the front end of the embodiment;

FIG. 4 shows a section on the line 4—4 in FIG. 2, partially broken away to show only of the front end of the embodiment;

FIG. 5 shows a bottom view of the embodiment, partially broken away to show only an intermediate portion of the embodiment;

FIG. 6 shows a section, partially broken away, taken on the line 6—6 in FIG. 5;

FIG. 13 shows an enlarged end view of the trunnion block for the eccentric drive;

FIG. 14 shows a partially broken away side view, sectioned on the line 14—14 in FIG. 15, of a modified drive system;

FIG. 15 shows a partially broken away top view of the drive system shown in FIG. 14;

FIG. 16 shows an enlarged end view of the bobbin support yoke; and

FIG. 17 shows a top view of the yoke shown in FIG. 16.

DETAILED DESCRIPTION OF PRESENT PREFERRED EMBODIMENTS

Figure 7:
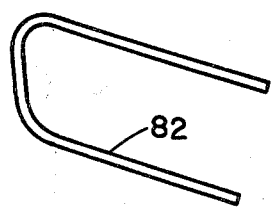
FIG. 7 shows a side view of an alternate wire guard which can be substituted for the side guards for the arms shown in FIGS. 1-4.

Referring now more particularly to the drawings, and initially to FIGS. 1–5, the illustrated flossing unit 1 has a main housing 2 attached by disengageable interlocks 73 and 74 (FIG. 3) to a removable head 3. A pair of spaced action arms 4 and 60 project beyond the housing head 3 to carry flossing thread 5. A portion 15 of floss 5 is suspended between the arms 4 and 60.

A supply of floss 5 is wound around a bobbin 23 journaled on bosses 83 and 84 of a resilient yoke 56 (FIGS. 16 and 17). The bobbin is removable from yoke 56 by springing apart bosses 83 and 84. A hole 64 through yoke 56 (FIG. 17) receives a rivet 85 attaching yoke 56 to housing 2 (FIG. 1).

A length of floss 5 extends from bobbin 23 past a set of opposed clamping surfaces 62 (FIGS. 2, 9 and 10) to the outside of arm 4, through port 34 in arm 4 to the innerside of arm 4, through port 68 in arm 4 to the outerside of arm 4, through port 69 in arm 4 (FIGS. 1 and 2) across an open space between arms 4 and 60 (FIG. 2) to a corresponding port 72 in arm 60 and then through ports 71 and 70 in arms 60 (FIG. 3) corresponding to ports 34 and 68, past a second set of opposed clamping surfaces 63 (FIGS. 2, 9 and 10) and through a port 17 to a cutter 46 mounted in a recess 45 in the outside of head 3 (FIGS. 5 and 6), where the leading end of the floss is severed by a V-shaped cutting edge on cutter 46 (FIG. 5). A floss threading needle may be used to facilitate threading in an easy manner throughout the unit. Enough of the cut leading end of floss 5 is exposed in recess 45 to permit grasping the cut end to pull a further supply of floss from bobbin 23.

Figure 9:
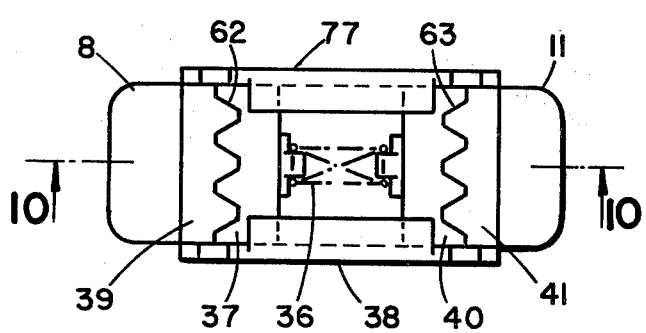
FIG. 9 shows an enlarged top view of the floss clamping assembly used in the embodiment shown in FIG. 2, (as viewed in the direction of lines 9—9 in FIG. 10)
Figure 10:
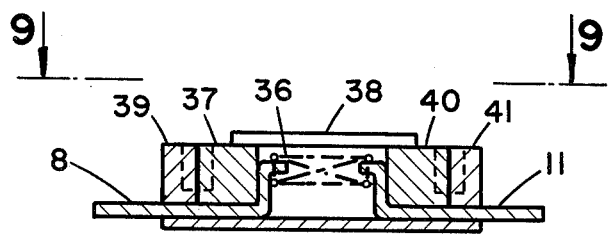
FIG. 10 shows a section taken on the line 10—10 in FIG. 9.

As shown in FIGS. 9 and 10, the first set of clamping surfaces 62 are provided by a clamping assembly 77 comprising opposite mating racks 37 and 39 mounted in a housing 38. A second set of clamping surfaces 63 are similarly provided by racks 40 and 41 in housing 38. Racks 39 and 41 are mounted in fixed positions and racks 37 and 40 are slideable toward each other and away from fixed racks 39 and 41 against the action of an intermediate compression spring 36, and are pressed by spring 36 toward racks 39 and 41 to clamp floss 5 firmly between surfaces 62 and 63. A pair of oppositely extending release members 8 and 11 are attached to racks 37 and 39, respectively, and the outer ends of these release members project outside of head 3 (FIG. 2). When these projecting ends are pressed toward each other the floss 5 is released for movement from bobbin 23 (FIG. 2) when its leading end in recess 45 (FIG. 5) is grasped and pulled past blade 46. When release member 11 is pressed but release member 8 is not, clamping surfaces 62 are closed to hold the floss on one side of arms 4 and 60 while clamping surfaces 63 on the other side are held open to permit the free end of the floss to be pulled tight. This tension causes and is maintained by a slight inward bending of stiffly resilient arms 4 and 60. Then release member 11 is released, and floss 5 is again clamped between surfaces 62 and 63.

The action arms 4 and 60 are pivotally mounted on a shaft 28 extending transversely through a hole 31 through a central portion of head 3 (FIGS. 2 and 3). Shaft 28 is held against lengthwise movement by snap lock rings 29 (FIG. 4) fitted in grooves in the shaft next to the outside of arms 4 and 60, and the outer ends of shaft 28 are aligned with ports 30 through the outer wall of head 3, to permit endwise insertion and removal of the shaft (FIGS. 1 and 2). The rear extensions of arms 4 and 60 are secured to a spacer block 35 therebetween (FIG. 4), and at their rear extremities mount a trunnion block 26 therebetween (FIGS. 2 and 4). A pair of cylindrical integral posts 44 and 58 extend from opposite sides of block 26 (FIG. 13) and are journaled in openings 54 and 59 through the rear extremities of the arms 4 and 60. A slot 43 through block 26 (FIG. 13) slidably receives an eccentric cylindrical stub 42 of drive coupling 24 (FIGS. 11 and 12) secured by set screw 25 to a drive shaft 32 driven by the reduction gear head 18 of a motor 19 (FIG. 4) powered by a battery pack 20 in housing 2 (FIG. 2). When shaft 32 rotates the eccentric stub 42 rotates and slides sidewise in slot 43 in trunnion block 26. This causes trunnion block 26 to move up and down (as viewed from the side as in FIG. 4), and this in turn causes arms 4 and 60 to rock back and forth on shaft 28 in the manner indicated by directional arrow 33 of FIG. 4. As a result, the suspended floss between arms 4 and 60 (FIG. 2) reciprocates laterally (substantially perpendicular to the length of the floss) with no endwise motion (parallel to the length of the floss), and for all practical purposes in a straight up and down path since the arc of its pivotal movement is only a few degrees and hence in an almost flat plane. The eccentricity of stub 42 ("X" in FIG. 11) is so small as to impart very limited rocking movement to arms 4 and 60, and the amplitude of movement of the suspended floss is very small relative to the length of the pivotal radius between the suspended floss 15 and the axis of shaft 28 on which arms 4 and 60 are pivoted.

Figure 8:
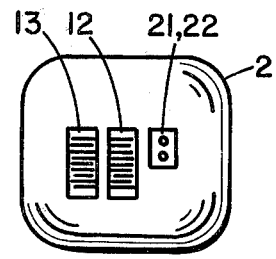
FIG. 8 shows a rear end view of the embodiment shown in FIGS. 1-6.

The battery pack 20 has a charging jack 21 accessible through a rear port 22 in housing 2 (FIGS. 2 and 8). An on-off switch 12 for the motor 19 is also mounted at the rear of housing 2, but this is wired in parallel with a pressure switch 7 (FIGS. 1 and 4). Unless pressure is maintained on switch 7 it overrides the "on" setting of switch 12 and shuts off motor 20. This is a safety feature and also helps to prevent accidental operation of clamping release members 8 and 11, which are located where it is hard to press them and at the same time to press switch 7. As shown in FIGS. 1 and 2, switch 7 is mounted at the top of the unit while clamp release members 8 and 11 project from the sides of the unit and are also closer to the front of the unit than switch 7.

The pair of action arms 4 and 60 are enclosed between a pair of guard members 6 and 61 (FIGS. 1–3). These guards are preferably of transparent plastic cast with in-turned peripherical flanges 6' and 61' for greater strength and to overlap the action arms and thereby protect the user from contact with the arms. The rear end of each guard has projecting prong 78 and 79 which are held in holes 80 and 81 in the head 3 (FIG.3). Other forms of arm guard can be used such as the metal wire member 82 shown in FIG. 7. This member has the same outline as the guards 6 and 61, and is mounted in the same holes 80 and 81 in head 3. Both types of guard members permit looking through them from the side, to see where the suspended floss is positioned relative to the teeth, especially in the case of front teeth.

As a further precaution, the exposed surfaces of the arms 4 and 60 are preferably given a rubberlike coating, to minimize trouble if the arms should come in contact with teeth or gums.

A satisfactory rate of reciprocation of suspended floss 15 is controlled primarily by selection of the degree of speed stepdown through the gear head 18, since conventional single speed electric motors rotate too fast for the purpose without such reduction. The rate at which the floss portion 15 moves up and down should be greater than the rate achieved through purely hand operation, for a proper balance of cleaning efficiency and safety.

Figure 11:
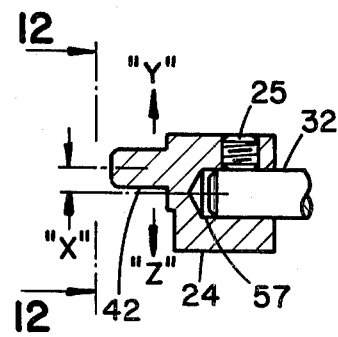
FIG. 11 shows an enlarged sectional view of the eccentric drive member shown in FIGS. 2 and 4, with a broken away end of the shaft which drives the eccentric member, said section being taken through the two axes of the eccentric member.
Figure 12:
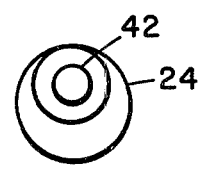
FIG. 12 shows an end view of the eccentric member shown in FIG. 11, as viewed in the direction indicated at 12—12 in FIG. 11.

The controlled or pre-set amplitude of reciprocal motion of the floss which is preferably less than that achieved by hand operation is safer for the protection of the soft dental tissue. This in combination with the higher stroke rate achieved by a power driven flossing unit provides a more efficient cleaning action. The amount of amplitude of reciprocation of suspended floss 15 is controlled primarily by selection of the ratio of distances from pivotal shaft 28 to suspended floss 15, on the one hand, and to trunnion block posts 44 and 58, on the other hand, and also by the selection of the amount of eccentricity of stub 42 (FIGS. 11 and 12).

As a further protective measure, the amplitude of reciprocation may be modified to introduce a resilient element capable of yielding when more than a predetermined resistance is encountered by the reciprocating suspended floss 15. As shown in FIGS. 14 and 15, this may be accomplished, for example, by replacing arms 4 and 60 with a pair of arms 48 and 48', which have the same structure forward of pivot shaft 28 (toward suspended floss 15) but which are shorter to the rear of pivot shaft 28, so that they no longer carry trunnion block 26. Instead, the rear extensions of arms 48 and 48' are joined by a spacer block 51 (which is shorter than the corresponding block 35 (shown in FIGS. 2 and 4), and a pair of yoke members 47 and 47' are pivoted on shaft 28 and extend past the shortened arm extensions to hold the posts 44 and 58 of trunnion block 26, which is moved up and down by eccentric stub 42 as earlier described. The yoke members 47 and 47' impart this motion to arms 48 and 48' through a pair of pre-loaded springs 49 and 50 compressed on opposite sides of spacer block 51 (FIG. 14). The opposite end of spring 49 is compressed against a plate 52 extending across and secured to the top edges of yoke members 47 and 47', and the opposite end of spring 50 is compressed against a plate 53 extending across and secured to the bottom edges of yoke members 47 and 47'. Thus, as plates of 52 and 53 are moved up and down by the action of eccentric stub 42 on trunnion block 26, this motion is transmitted to spacer block 51 and arms 48 and 48' alternately through springs 49 and 50 as the up and down motion alternates (in the directions indicated at "Y" and "Z" in FIG. 11). The resilience of springs 49 and 50 is thus available to absorb unusual resistance to movement of arms 48 and 48' before there is time for the user to react and stop the motor.

The unit is thus arranged for convenient and safe use and this is further enhanced by mounting a light source 10 in a recess located at the front of head 3 and covered by a protective lense 9. An on-off switch 13 at the rear of unit (FIG. 8) controls light source 10. The surface of the cavity around the light source is reflective and so shaped as to direct the light generally toward the suspended floss portion 15, so that it will illuminate and make more visible to the user the portion of the mouth and teeth where the suspended floss 15 is being inserted and put into use.

It may be desirable to clean off the suspended floss portion 15 under running water after use, preliminary to pulling more floss through the unit. Hence, the lense 9 is sealed around the light source cavity to prevent entry of outside water, and rubber sealing boots 55 and 67 prevent outside water from passing through the ports in head 3 which the arms 4 and 60 project (FIG. 2).

The versatility of the system may be enhanced by providing removable heads 3 of different sizes for use with a single housing 2. This would enable persons of different mouth and tooth sizes, such as children and adults, to use a single drive unit for a set of different sized heads. The drive coupling 24 may also be replaced with another one of different eccentricity to modify the amplitude of reciprocation of arms 4 and 60, in order to meet special dental requirements of some users.

While present preferred embodiments and practices of the invention have been illustrated and described, it will be understood that the invention may otherwise be embodied and practiced within the scope of the following claims.

What is claimed is:

1. Powered apparatus for cleaning interproximal tooth surfaces with dental floss, comprising an elongated hollow body having a rear end and a front end, a motor mounted adjacent the rear end of the body, a pair of spaced arms, means within the body pivotally mounting said arms on the body to rock about an axis extending transversely of the length of the body, said arms having rear portions extending from said axis toward the motor and longer forward portions extending from said axis to project beyond the front end of the body, means connecting said arms so that they move together as a unit, drive means connecting the motor to rock the arms about the said pivotable axis to a limited extent, said drive means comprising means having a slot therein elongated generally parallel to said pivotal axis, means connecting said slotted means to the rear portion of the arms, an element extending slideably into said slot, means rotatable by the motor about an axis of rotation extending in the same direction as the elongation of said body, said rotatable means mounting said element to extend parallel to, but eccentrically offset, relative to said access of rotation, means to suspend the length of floss between the projecting ends of the forward portion of the arms, said suspended floss being carried by the arms without endwise movement, and the distance between the suspended floss and the pivotal access being very much longer than the amplitude of limited movement of the arm ends where the floss is suspended, whereby the suspended floss is caused to reciprocate laterally in a substantially flat plane, and resilient means in said connection between the slotted means and the rear portions of the arms, said resilient means being connected to transmit rocking motion to the arms, whereby the arm drive can yield when the suspended floss encounters more than a predetermined resistance.

2. Apparatus according to claim 1, in which the predetermined resistance is such as to provide periodontal structure protection.

3. Apparatus according to claim 1, comprising a light source mounted within the front end of the body and between the forward portions of the arms, and means directing light from the light source toward the suspended floss, whereby light may be directed toward the area where the floss is to be used.

4. Powered apparatus for cleaning interproximal tooth surfaces with dental floss, comprising an elongated hollow body having a rear end and a front end, a motor mounted adjacent the rear end of the body, a pair of spaced arms, means within the body pivotally mounting said arms on the body to rock about an axis extending transversely of the length of the body, said arms having rear portions extending from said axis toward the motor and longer forward portions extending from said axis to project beyond the front end of the body, means connecting said arms so that they move together as a unit, drive means connecting the motor to rock the arms about the said pivotable axis to a limited extent, said drive means comprising means having a slot therein elongated generally parallel to said pivotal axis, means connecting said slotted means to the rear portion of the arms, an element extending slideably into said slot, means rotatable by the motor about an axis of rotation extending in the same direction as the elongation of said body, said rotatable means mounting said element to extend parallel to, but eccentrically offset, relative to said access of rotation, means to suspend the length of floss between the projecting ends of the forward portion of the arms, said suspended floss being carried by the arms without endwise movement, and the distance between the suspended floss and the pivotal access being very much longer than the amplitude of limited movement of the arm ends where the floss is suspended, whereby the suspended floss is caused to reciprocate laterally in a substantially flat plane, and stationary members fixedly mounted on the body and extending next to the outside of the projecting ends of the arms, to guard against contact of the cheeks, tongue and teeth with the moving arms.

5. Apparatus according to claim 4, wherein said guard members have flanges overlapping the projecting ends of the arms.

6. Powered apparatus for cleaning interproximal tooth surfaces with dental floss, comprising an elongated body, a pair of spaced arms having ends projecting beyond one end of the body, means mounting said arms on the body for pivotal movement about end axis extending transversely of the length of said body, means connecting said arms so that they move together as a unit, a motor, means connecting the motor to rock the arms about the said pivotal axis to a limited extent, and means to suspend a length of floss between the projecting ends of the arms, the distance between the suspended floss of the pivotal axis being very much longer than the amplitude of limited movement of the arm ends where the floss is suspended, whereby the suspended floss in caused to recriprocate laterally in a substantially flat plane, said arms having rear extensions beyond the pivotal mounting means, and said motor connecting means comprising means mounted for independent movement, slotted means carried by said independently movable means, rotatable eccentric means engaging said slotted means, and spring means between said arm rear extensions and said independently movable means, whereby the arm drive can yield when the suspended floss encounters more than a predetermined resistance.

7. Powered apparatus for cleaning interproximal tooth surfaces with dental floss, comprising an elongated body, a pair of spaced arms having ends projecting beyond one end of the body, means mounting said arms on the body for pivotal movement about an axis extending transversely of the length of said body, means connecting said arms so that they move together as a unit, a motor, means connecting the motor to rock the arms about the said pivotal axis to a limited extent, and means to suspend a length of floss between the projecting ends of the arms, the distance between the suspended floss of the pivotal axis being very much longer than the amplitude of limited movement of the arm ends where the floss is suspended, whereby the suspended floss in caused to recriprocate laterally in a substantially flat plane, including a light source in the end of the body from which the arms project, a lens over the light source, and means sealing the lens to the body against the entry of water during washing of used floss.

* * * * *